United States Patent [19]

Brooks

[11] Patent Number: 5,312,381
[45] Date of Patent: May 17, 1994

[54] OSTOMY POUCH COUPLING HAVING CONTINUOUS HELICAL THREADS

[76] Inventor: James P. Brooks, 3404 Brantford Rd., Toledo, Ohio 43606

[21] Appl. No.: 27,020
[22] Filed: Mar. 5, 1993
[51] Int. Cl.⁵ ............................................. A61F 5/44
[52] U.S. Cl. .................................. 604/338; 604/332; 604/342; 604/339
[58] Field of Search ............... 604/332, 338, 339, 342, 604/345

[56] References Cited

U.S. PATENT DOCUMENTS

| | | | |
|---|---|---|---|
| 2,818,069 | 12/1957 | Fenton | 604/338 |
| 3,021,843 | 2/1962 | Perry | 604/339 |
| 3,076,458 | 2/1963 | Mason | 604/339 |
| 3,736,934 | 6/1973 | Hennessy | 604/342 |
| 3,826,262 | 7/1974 | Blackwood | 604/339 |
| 4,109,657 | 8/1978 | Carrington | 604/338 |
| 4,816,027 | 3/1989 | Gilchrist et al. | 604/339 |
| 4,846,798 | 7/1989 | Holtermann et al. | 604/339 |
| 4,865,594 | 9/1989 | Thomas | 604/332 |

*Primary Examiner*—Randall L. Green
*Assistant Examiner*—Rob Clarke
*Attorney, Agent, or Firm*—Marshall & Melhorn

[57] ABSTRACT

An ostomy coupling device comprises a faceplate for placing over the stoma including a neck having outwardly facing threads, and a generally cylindrically shaped screw coupling having threads on the inner surface thereof. The narrow portion of an ostomy pouch is placed over the neck, and the screw coupling is thereafter rotated onto the neck, whereby the aperture collar of the pouch is conformed to the space between the matching threads of the screw coupling and faceplate, thereby providing a seal between the pouch and the stomal aperture.

6 Claims, 2 Drawing Sheets

OSTOMY POUCH COUPLING HAVING CONTINUOUS HELICAL THREADS

BACKGROUND OF THE INVENTION

1. Field of the Invention

This invention relates to couplings for ostomy devices, and more particularly, to a helical screw type coupling for securing an ostomy pouch to an ostomy device base plate.

2. Summary of the Invention

Ostomy pouches are used to collect body wastes from patients having a stoma resulting from an ileostomy, colostomy, or similar surgical procedure. Generally, drainage or discharge from the digestive system is routed outside the body by extending the remaining distal portion of the large or small intestine through the abdominal wall, and collecting the drainage or discharge in an ostomy pouch which is secured to the patient's body via a coupling mechanism.

U.S. Pat. No. 3,339,546 discloses a coupling mechanism whereby an ostomy pouch is secured to the patient by attaching it to an adhesive backed label through which a central opening can be made to receive the stoma.

Generally, an ostomy coupling system involves at least two coupling rings. The first ring or faceplate is bonded to a dressing, which contacts the body in the area surrounding the stoma, and is held in place by an adhesive and a belt encircling the trunk of the patient. The second ring, which is adapted to securely connect in some fashion to the first ring, has bonded thereto one wall of an ostomy pouch having therein a hole to align with the stomal opening. Such devices are disclosed for example in U.S. Pat. Nos. 4,710,182; 4,610,676; 4,460,363 and 3,970,085. Generally, these coupling rings of the prior art are coupled together by applying a significant force to press the rings together, thereby causing pain in the sensitive region around the stoma.

While the hereinabove described coupling systems have been found useful, it would be desirable to improve the method of attaching an ostomy pouch to the body, by simplifying the coupling element so as to make it easier to affix the pouch to the faceplate around the stomal opening. Additionally, it would be advantageous to manufacture a coupling device using simple molding equipment. Moreover, an improved ostomy device should employ a pouch which is not required to be bonded to one of the coupling members, and which could be easily produced for example by thermoplastic sheet extrusion and heat sealing techniques. The bonding of the pouch to one of the coupling members adds considerable cost to the use of the device. The ability to conveniently mount a simple and inexpensive pouch on a reusable coupling would result in considerable savings.

SUMMARY OF THE INVENTION

In accordance with the present invention there is provided an ostomy coupling apparatus, in an ostomy device of the type generally including a faceplate surrounding the stoma, an ostomy pouch for collecting digestive system drainage, and a coupling for securing the pouch to the faceplate. The faceplate includes an aperture extending through the center thereof for communication with the stoma. An annular recess in the faceplate is adapted to receive a skin barrier adhesive wafer for sealably contacting said faceplate against the region of the patient's skin immediately surrounding the stoma. An outwardly facing helically threaded neck extends from the outer surface of the faceplate and connects to a screw coupling provided with a cylindrical wall having helical threads formed on the inwardly facing surface thereof adapted to engage the threaded neck of said faceplate.

The ostomy pouch may be secured to the faceplate by positioning the narrow opening of the pouch such that its inner surface is adjacent the threaded neck of the faceplate. The inwardly facing helical threads of the screw coupling secure the pouch and against the threaded neck of the faceplate, thereby providing a seal between the inner surface of the pouch and the aperture receivably surrounding the stoma.

Such a device may be manipulated using only moderate force, such as can be applied easily by an elderly or infirm person. The present invention is most suitable as a coupling for colostomy and ileostomy devices.

Two embodiments are shown for securing the device to the patient's body. In the first embodiment, the face plate is provided with slots for securing a belt. The belt extends around the body to secure the device about the stoma. In the second embodiment, an adhesive is used to secure the face plate. The adhesive face plate eliminates the need for a belt and provide a tighter seal about the stoma.

BRIEF DESCRIPTION OF THE DRAWINGS

The novel features which are considered characteristic of the invention are set forth with particularity in the claims. The invention itself, however, both as to structure and method of use, will best be understood from the accompanying description of a specific embodiment, when read in connection with the accompanying drawings, in which:

DETAILED DESCRIPTION OF THE PREFERRED EMBODIMENT

Figure 1:
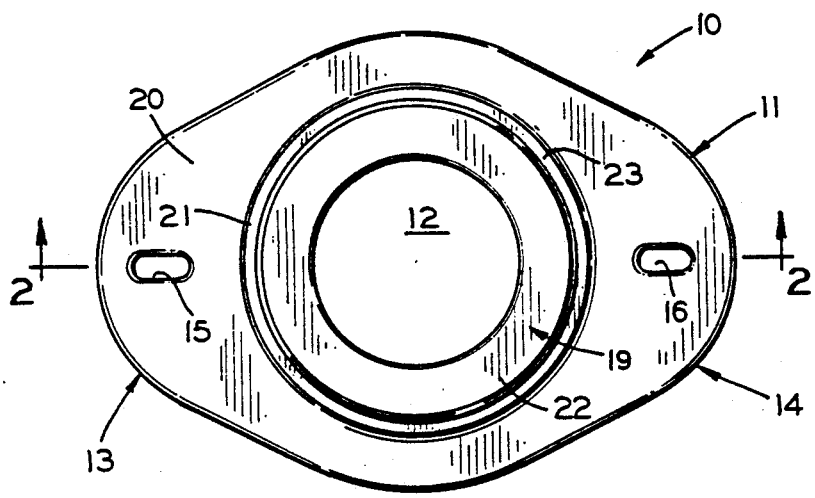
FIG. 1 is a top plan view of one embodiment of a faceplate, according to the present invention.
Figure 2:
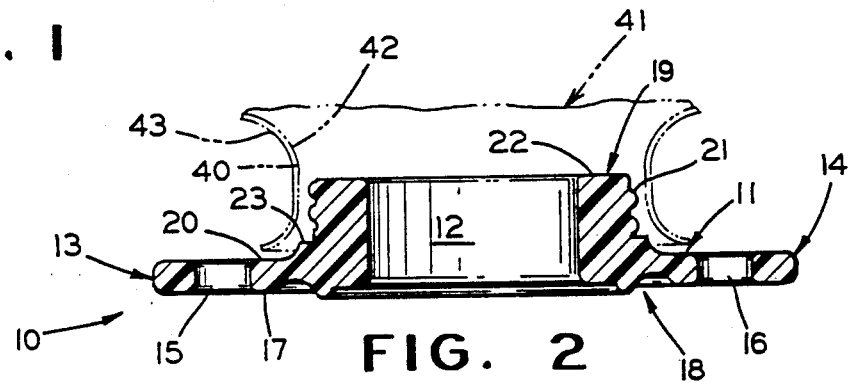
FIG. 2 is a sectional view, taken along line 2—2 of FIG. 1, illustrating the threaded neck of the faceplate, and indicating in broken lines the positioning of the narrow portion of an ostomy pouch just prior to its coupling to the faceplate.

FIGS. 1 and 2 illustrate an ostomy device faceplate, indicated generally at 10, preferably made from a resilient and deformable plastic material such as for example a low density polyethylene, a polypropylene, a polyurethane, or the like, including a generally elliptical body 11 having a central circular stomal aperture 12 extending through the body 11. Wing portions 13 and 14 contain elongated slots 15 and 16, respectively, for adjustably fastening the faceplate 10 to the ends of a belt (not shown) to encircle the trunk of a patient's body and assist in securing the faceplate 10 against the skin.

A first surface 17 of the faceplate 10 is placed in apposition to the patient's skin during use of the ostomy device. An annular recess 18 is formed in the surface 17 of the faceplate 10, and is positioned concentric with and radially outward from the stomal aperture 12. The annular recess 18 is adapted to receive a skin barrier adhesive wafer (not shown) which assists in sealing the ostomy device against the patient's skin and fixing the location of aperture 12 coaxially with the stoma.

A neck 19 extends normally away from a second surface 20 of the faceplate 10, and includes outwardly facing helical threads 21, a top 22 located at the distal portion of the neck 19 opposite the faceplate, and a flared shoulder 23 near the intersection of the outwardly facing helical threads 22 and the faceplate 10. The shoulder presents a generally annular surface normal to the axis of the faceplate aperture 12. The neck 19 is coaxial with the aperture 12, and defines the outer surface against which an ostomy pouch 41 is to be placed for coupling.

Figure 3:
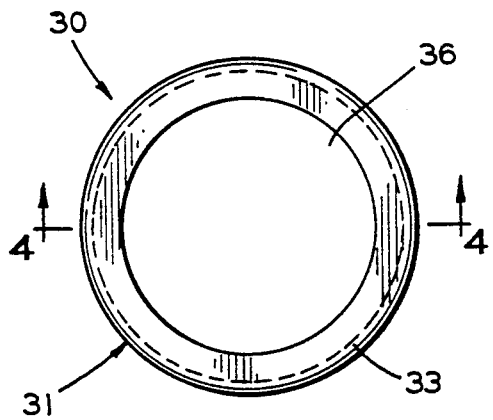
FIG. 3 is a top plan view of one embodiment of a screw connector, according to the present invention.
Figure 4:
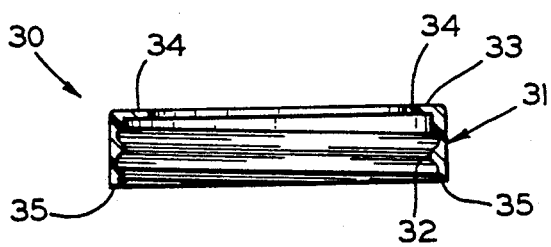
FIG. 4 is a sectional view, taken along line 4—4 of FIG. 3, illustrating the threads on the inwardly facing surface of the screw connector.

FIGS. 3 and 4 illustrate an ostomy device screw coupling, indicated generally at 30, preferably made from a rigid plastic material such as for example a polyvinylidine chloride, a polyester, a polycarbonate, a polyurethane, or the like. The screw coupling 30 is generally cylindrical in configuration, and includes comprising a continuous wall 31, defining an aperture 36, having helical threads 32 on the inwardly facing surface thereof. The wall 31 of the screw coupling additionally includes a top surface 33 at the end of the wall 31 opposite the faceplate when the ostomy device is assembled, and a bottom surface 35 opposite the top surface 33. The top surface 33 includes a radially inwardly directed lip 34. The screw coupling 30 is manufactured so as to allow the threads 32 to generally conform to the configuration of the threaded neck 19 of the faceplate 10. However, the threads 32 are formed so as to only loosely engage the threaded neck 19, to provide adequate space therebetween for the positioning and deformation of the aperture collar 40 of the ostomy pouch 41.

The ostomy pouch 41 is a sealed enclosure having a single opening defined by aperture collar 40, as illustrated in broken lines in FIG. 2, just prior to being coupled to the faceplate 10. The pouch 41 is generally formed of a relatively thin walled, flexible thermoplastic material such as for example low density polyethylene, polyvinylidine chloride, or the like. When the pouch 41 is coupled to the faceplate 10, the inner surface 42 at the aperture collar 40 of the pouch 41 is positioned adjacent the outwardly facing helical threads 21. The outer surface 43 at the aperture collar 40 of the pouch 41 is thereafter contacted by the threads 32 of the screw coupling 30, and the aperture collar 40 of the pouch 41 is caused to conform with the shape of both threaded surfaces by deformation therebetween upon the rotational engagement of the screw coupling 30 onto the neck 19. It is apparent, when attaching the pouch 41 to the ostomy device by properly positioning the pouch and thereafter applying the screw coupling to the faceplate, that the aperture collar 40 of the pouch 41 may first be passed through the aperture 36 of the screw coupling 30 before the inner surface 42 of the aperture collar 40 of the pouch 41 is positioned adjacent the threads 21 of the faceplate 10. Alternatively, the screw coupling 30 may be threaded over the ostomy pouch 41 by passing the pouch 41 through the aperture 36.

Figure 5:
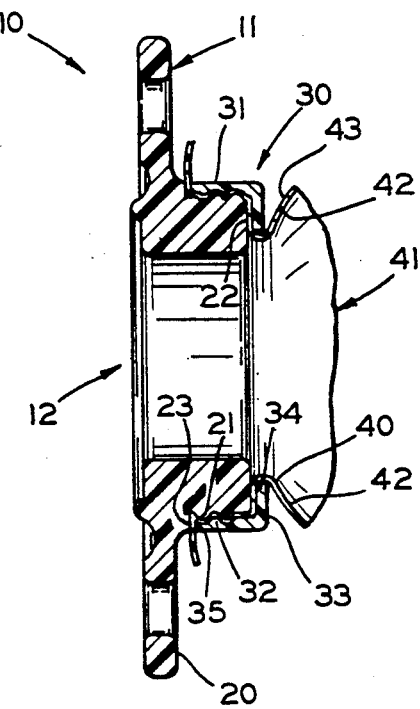
FIG. 5 is an enlarged sectional view of the assembled faceplate and screw connector, illustrating the narrow portion of the pouch conformed therebetween, according to the present invention.

Referring now to FIG. 5, there is shown the assembled ostomy pouch coupling device, including the faceplate 10, and the screw coupling 30, having the aperture collar 40 of the ostomy pouch 41 conformed therebetween. When assembled, a seal is provided between the inner surface 42 of the ostomy pouch 41 and the aperture 12 of the faceplate 10, by the conformation of the aperture collar 40 of the pouch 41 between the threads 32 of the screw coupling 30 and the threads 21 of the faceplate 10. Preferably, the integrity of the seal may be improved by further rotation of the screw coupling 30, until the aperture collar 40 of the pouch 41 is conformed and intimately contacted between the bottom 35 of the screw coupling 30 and the shoulder 23 of the faceplate 10, and/or between the lip 34 of the screw coupling 30 and the top 22 of the faceplate 10.

Since the screw coupling 30 is not integrally formed as part of the pouch 41, it is possible to use the same screw coupling for an extended period of time. Instead of purchasing the pouches with couplings, a very expensive proposition, the screw coupling 30 may be used with fairly inexpensive pouches 41 which can be manufactured and sold at a competitive bulk price. In addition, the pouches 41 may be disposed of by removing the screw coupling 30, folding or sealing the collar 40 of the pouch 41 and flushing the pouch 41 down a conventional toilet.

Figure 6:
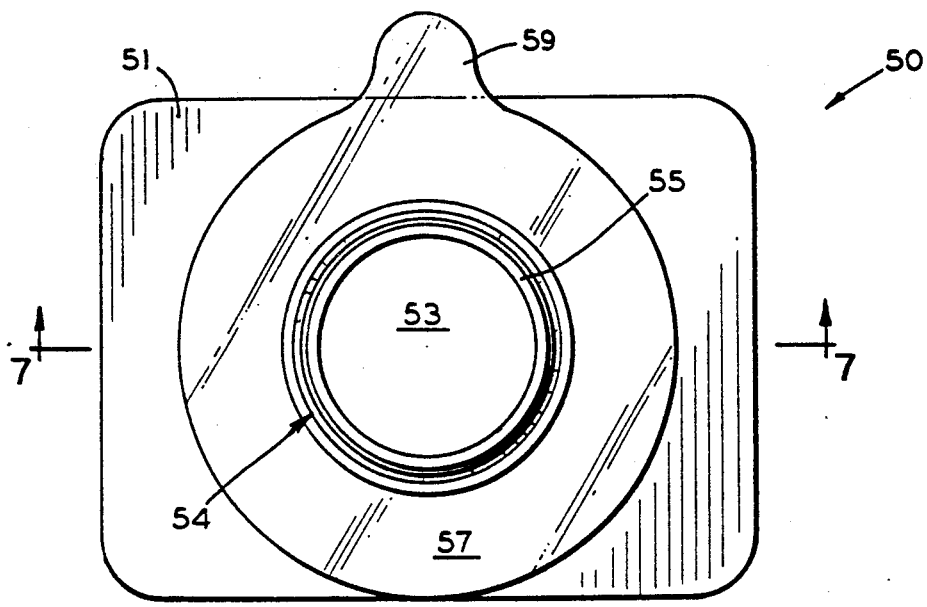
FIG. 6 is a top plan view of a second embodiment of a faceplate, according to the present invention.
Figure 7:
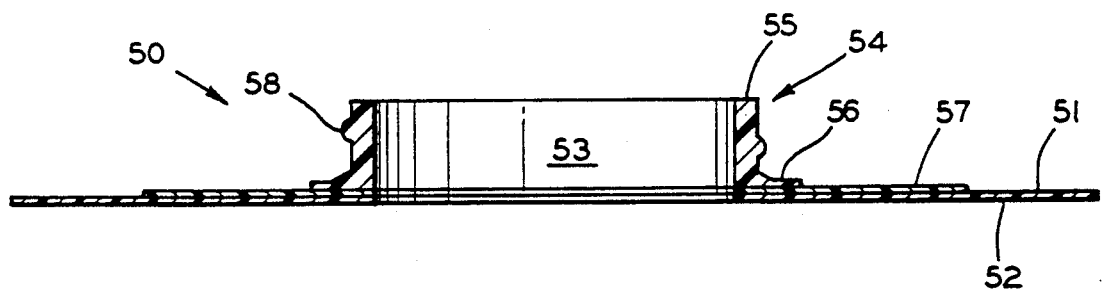
FIG. 7 is a sectional view, taken along line 7—7 of FIG. 6, illustrating the threaded neck of the faceplate.

FIGS. 6 and 7 show an ostomy device faceplate 50 with an alternative means for securing the faceplate 50 to the patient's body. The flexible faceplate 50 includes an outer surface 51 and an inner surface 52 having a central circular stomal aperture 53. The inner surface 52 is coated with a pressure sensitive adhesive of sufficient strength to seal the ostomy faceplate 50 against the patient's skin and fixing the location of the aperture 53 with the stoma. The adhesive surface 52 is provided with a backing (not shown) which is removed to apply the faceplate 50 to the patient's skin.

The adhesive surface 52 provides a tight seal at the skin. The belts are difficult to tighten and have faceplate may have a tendency to slip, which compromises the skin seal of the faceplate. The adhesive surface 52 provides such a tight seal that the patient may bathe and even swim without leaks occurring around the aperture 53.

The neck 54 includes a top 55 located at the distal portion of the neck 54 and a flared shoulder 56. A base film 57 is used to secure the neck 54 to the outer surface 51 of the faceplate 50. A heat selling process or other bonding process is used to join the neck 54 to the upper surface 51 and base film 57. The base film 57 and neck 54 are coaxial with the aperture 53.

A tab 59 is provided to assist in removing the faceplate 50 from the skin of the patient. The faceplate 50 needs to be changed at regular intervals when the faceplate becomes unsanitary or when the seal between surface 52 and the patient's skin begins to break down.

The faceplate 50 utilizes the same screw coupling 30 as shown in FIGS. 3-4. The pouch 41 is secured by the coupling 30 about the neck 54 of faceplate 50 in the same manner as described above. The present embodiment provides excellent sealing capabilities between both the pouch 41 and the neck 54 coupling 30, and the faceplate 50 and the skin of the patient.

While certain representative embodiments and details have been shown for the purpose of illustrating the present invention, it will be apparent to those ordinarily skilled in the art that various changes in applications can be made therein, and that the invention may be practiced otherwise than as specifically illustrated and described without departing from its spirit and scope.

What is claimed is:

1. An ostomy coupling apparatus generally including a faceplate surrounding a stoma, an ostomy pouch for collecting digestive system drainage, and a coupling for securing the pouch to the faceplate, the improvement comprising:
   a) a faceplate made from a resilient and deformable material, having an aperture extending through the center thereof for communication with the stoma and including a first surface provided with means for sealably contacting said faceplate against the patient's skin surrounding the stoma, and an outwardly facing helically threaded neck extending from a second surface of said faceplate opposite the first surface and coaxial with the aperture, the threaded neck including an annular shoulder generally located where the threaded neck and said faceplate are joined and a top surface at the distal portion of the neck opposite said faceplate; and
   b) a screw coupling, including a cylindrical wall having continuous helical threads formed on an inwardly facing surface thereof adapted to engage the threaded neck of said faceplate, a bottom surface located at the end of the cylindrical wall to engage the shoulder on the neck of said faceplate, and a lip extending radially inwardly from the end of the wall opposite the bottom surface to engage the top surface at the distal portion of the neck; whereby the ostomy pouch, having an inner surface and an aperture collar adapted for connecting to said faceplate, may be secured to the faceplate by positioning the aperture collar of the pouch such that the inner surface is adjacent the threaded neck of said faceplate, and thereafter rotatably engaging the inwardly facing continuous helical threads of said screw coupling over the threaded neck of said faceplate, and such that the inner surface of the ostomy pouch is sealed by the engagement of the collar of the ostomy pouch between the top surface of the neck and the lip of the screw coupling, between the helical threads of said screw coupling and the helical threads of the neck, and between the bottom surface of said screw coupling and the shoulder of said faceplate and said continuous helical threads of said screw coupling continue at least 360 degrees around the cylindrical wall.

2. The ostomy coupling apparatus defined in claim 1 wherein said means for sealably contacting said faceplate against the patient's skin includes an annular recess in the first surface of said faceplate and concentric with the aperture therethrough, adapted to receive a skin barrier adhesive wafer.

3. The ostomy coupling apparatus defined in claim 1 wherein said means for sealably contacting said faceplate against the patient's skin includes an adhesive means applied to the first surface of said faceplate about said aperture whereby a removable seal is formed between said faceplate and the patient's skin surrounding the stoma.

4. The ostomy coupling apparatus defined in claim 1 wherein said faceplate is formed of a material selected from the group consisting of low density polyethylene, polypropylene, and polyurethane; and said screw coupling is formed of a material selected from the group consisting of polyvinylidine chloride, polyester, polycarbonate and polyurethane.

5. The ostomy coupling apparatus defined in claim 1 wherein the helical threads on said screw coupling have a slightly larger diameter than the helical threads on said neck to provide adequate space therebetween for the positioning and deformation of the aperture collar on the ostomy pouch.

6. An ostomy coupling apparatus generally including a faceplate surrounding a stoma, an ostomy pouch for collecting digestive system drainage, and a coupling for securing the pouch to the faceplate, the improvement comprising:
   a) a faceplate made from a resilient and deformable material, having an aperture extending through the center thereof for communication with the stoma and including a first surface provided with means for sealably contacting said faceplate against the patient's skin surrounding the stoma, a neck having an outward facing, continuous helical thread, the neck extending from a second surface of said faceplate opposite the first surface and coaxial with the aperture, the threaded neck including an annular shoulder generally located where the threaded neck and said faceplate are joined and a top surface at the distal portion of the neck opposite said faceplate; and
   b) a screw coupling, including a cylindrical wall having continuous helical threads formed on an inwardly facing surface thereof, the threads of said screw coupling having a slightly larger diameter than the threads of the neck of said faceplate to facilitate the positioning and engagement of the ostomy pouch between the helical threads of the neck and said screw coupling, a bottom surface located at the end of the cylindrical wall to engage the shoulder on the neck of said faceplate, and a lip extending radially inwardly from the end of the wall opposite the bottom surface to engage the top surface at the distal portion of the neck; whereby the ostomy pouch, having an inner surface and an aperture collar adapted for connecting to said faceplate, may be secured to the faceplate by positioning the aperture collar of the pouch such that the inner surface is adjacent the threaded neck of said faceplate, and thereafter rotatably engaging the inwardly facing helical threads of said screw coupling over the threaded neck of said faceplate, and such that the inner surface of the ostomy pouch is sealed by the engagement of the collar of the ostomy pouch between the top surface of the neck with the lip of the screw coupling, between the helical threads of said screw coupling and the helical threads of the neck, and between the bottom surface of said screw coupling and the shoulder of said faceplate and said continuous helical threads of said screw coupling continue at least 360 degrees around the cylindrical wall.

* * * * *